United States Patent [19]
Grierson et al.

[11] Patent Number: 5,530,190
[45] Date of Patent: Jun. 25, 1996

[54] DNA CONSTRUCTS CONTAINING THE GENE FOR ACC OXIDASE, CELLS AND PLANTS DERIVED THEREFROM

[75] Inventors: Donald Grierson, Loughbrough; Andrew J. Hamilton, Nottingham; Grantley W. Lycett, Loughbrough, all of England

[73] Assignee: Imperial Chemical Industries PLC, London, England

[21] Appl. No.: 133,834

[22] Filed: Oct. 12, 1993

Related U.S. Application Data

[63] Continuation of Ser. No. 793,450, filed as PCT/GB90/01072, Jul. 12, 1990, Pat. No. 5,365,015.

[30] Foreign Application Priority Data

Jul. 14, 1989 [GB] United Kingdom ............... 89162213

[51] Int. Cl.$^6$ ............................ A01H 4/00; C12N 15/82; C12N 15/29
[52] U.S. Cl. ................... 800/205; 435/320.1; 435/240.4; 435/172.3; 800/DIG. 44
[58] Field of Search ............................. 435/172.3, 320.1, 435/240.4; 800/205, 250, DIG. 44; 536/23.6

[56] References Cited

U.S. PATENT DOCUMENTS

| | | | |
|---|---|---|---|
| 4,801,540 | 1/1989 | Hiatt et al. | 435/172.3 |
| 5,034,323 | 7/1991 | Jorgensen et al. | 435/172.3 |
| 5,107,065 | 4/1992 | Shewmaker et al. | 800/205 |

FOREIGN PATENT DOCUMENTS

| | | |
|---|---|---|
| 0240208 | 10/1987 | European Pat. Off. . |
| 0271988 | 6/1988 | European Pat. Off. . |

OTHER PUBLICATIONS

Holdsworth et al, Plant Molecular Biology, 11:81–88 (1988).
Weintraub et al, Trends in Genetics, pp. 22–25 (Jan., 1985).
Theologis et al, UCLA Symposia, Mol. Cell. Biol., 129;pp.289–299(Apr., 1989).
Hamilton et al, Biological Abstracts, BR:39:65911 and 1990 Annual Meeting of the Society for Experimental Biology, J. Exp. Bot., 41:5–5 (1990).
Biggs et al, Chemical Abstracts, vol. 109 (1988), abstract 3936q and Physiol. Plant., 72(3);572–8 (1988).
J. Mol et al, Tibtech, 7:148–153 (Jun. 1989).
Grierson et al, Plant Biology, vol. 4, Tomato Biotechnology, Symposium (Aug., 1986).
Holdsworth et al, Nucleic Acids Research, 15(2):731–739 (1987).
Hamilton et al, Nature, 346:284–287 (Jul., 1990).
Holdsworth et al, Nucleic Acids Research, 15(24):10600 (1987).
Napoli et al, The Plant Cell, 2:279–289 (Apr. 1990).
van der Krol et al, The Plant Cell, 2:291–299 (Apr. 1990).
van der Krol et al, Plant Molecular Biology, 14:457–466 (1990).
Sato et al, The Journal of Biological Chemistry, 266(6):3752–3759 (1991).
Tigchelaar et al, Tomato Fruit Ripening Mutants to Enhance Storage Life, 123–136 (1989).
Smith et al, Nature, 334:724–726 (Aug. 1988).
Holdsworth et al, Nucleic Acids Research, 15(2):731–739 (1987).
Herskowitz, Nature, 329(17):219–222 (Sep. 1987).
Wang, et al. (1991) Plant Physiol. 96:1000–1001.
Michael, et al (1993) in Pech, et al., eds., Cellular and Molecular Aspects of the Plant Hormone.
Ethylene, pp. 298–303, Kluiver Academic Publishers, The Netherlands.
Murray, et al. (1993) Postharvest Biology and Technology 2: 301–313.
Picton, et al. (1993) The Plant Journal 3(3): 469–481.
Hamilton, et al. (1990) Nature 346:284–287.
Van der Straeten, et al. (1990) Proc. Natl. Acad. USA 87:4859–4863.
Sato, et al. (Sep. 1989) Proc. Natl. Acad. Sci. 86:6621–6625.

*Primary Examiner*—Che S. Chereskin
*Attorney, Agent, or Firm*—Cushman Darby & Cushman

[57] ABSTRACT

DNA constructs which inhibit ethylene production in plants comprise a transcriptional initiation region operative in plants for transcribing a DNA sequence encoding an RNA sequence (which may be inverted) complementary to a substantial run of bases showing substantial homology to an mRNA encoding an enzyme involved in ethylene biosynthesis: also plant cells comprising such constructs and plants derived therefrom showing reduced ethylene production.

15 Claims, 10 Drawing Sheets

FIG. 1A

```
ATTCATCTCTTCAATCTTTTGTATTCATTCACATATTCTATTTATTCAATACAC
       10        20        30        40        50
                                 M  E  N  F
TTAGGAAAACACTTTACCAAGAAATTAAGATGGAGAACTT
       60        70        80        90

P  I  I  N  L  E  K  L  N  G  D  E  R  A  N  T
CCCAATTATTAACTTGGAAAAGCTCAATGGAGATGAGAGAGCCAACACCA
       100       110       120       130       140

M  E  M  I  K  D  A  C  E  N  W  G  F  F
TGGAAATGATCAAAGATGCTTGTGAGAATTGGGGCTTCTT
       150       160       170       180

E  L  V  N  H  G  I  P  H  E  V  M  D  T  V  E
TGAGTTGGTGAACCATGGAATTCCACATGAAGTAATGGACACAGTAGAGA
       190       200       210       220       230

K  M  T  K  G  H  Y  K  K  C  M  E  Q  R
AAATGACAAAGGGACATTACAAGAAGTGCATGGAACAGAG
       240       250       260       270
```

FIG. 1B

```
  F   K   E   L   V   A   S   K   G   L   E   A   V   Q   A   E
GTTTAAGGAACTAGTGGCCAAGTAAGGGGACTTGAGGCTGTGTTCAAGCTGAGG
            280             290             300             310         320

V   T   D   L   D   W   E   S   T   F   F   L   R   H
TTACTGATTTAGATTGGGAAAGCACTTTCTTCTTGCGCCA
            330             340             350             360

L   P   T   S   N   I   S   Q   V   P   D   L   D   E   E   Y
TCTTCCTACTTCTAATATCTCAAGTACCCGATCTTGACGAAGAATACA
            370             380             390             400         410

R   E   V   M   R   D   F   A   K   R   L   E   K   L
GAGAGGTGATGAGAGATTTTGCTAAAAGATTGGAGAAATT
            420             430             440             450

A   E   E   L   L   D   L   L   C   E   N   L   G   L   E   K
GGCTGAGGAGTTACTTGACTTACTCTGTGAAAATCTTGGACTTGAAAAAG
            460             470             480             490         500

G   Y   L   K   N   A   F   Y   G   S   K   G   P   N
GTTACTTGAAAAATGCCTTTTATGGATCAAAAGGTCCCAA
            510             520             530             540
```

FIG. 1C

```
  F   G   T   K   V   S   N   Y   P   P   C   P   K   P   D   L
CTTGGTACTAAAGTTAGCAACTATCCACCATGTCCTAAGCCCGATTTGA
            550             560             570             580             590

I   K   G   L   R   A   H   T   D   A   G   G   I   I
TCAAGGGACTCCGCGCTCATACAGAGACGCAGGAGGCATCAT
            600             610             620             630

L   F   Q   D   D   K   V   S   G   L   Q   L   L   K   D
ACTTCTGTTCCAAGATGACAAAGTGAGTGGCCTTCAACTCCTCAAAGACG
            640             650             660             670             680

E   Q   W   I   D   V   P   P   M   R   H   S   I   V
AGCAATGGATCGATGTTCCTCCCATGCGCCACTCTATTGT
            690             700             710             720

V   N   L   G   D   Q   L   E   V   I   T   N   G   K   Y   K
GGTTAACCTTGGTGACCAACTTGAGGTGATCACTAACGGGAAGTACAAGA
            730             740             750             760             770

S   V   L   H   R   V   I   A   Q   T   D   G   T   R
GTGTGCTGCACAGAGTAATTGCACAAACAGACGGGACACG
            780             790             800             810
```

FIG. ID

```
  M  S  L  A  S  F  Y  N  P  G  S  D  A  V  I  Y
AATGTCATTAGCCTCATTTACAATCCAGGAAGTGATGCAGTAATATATC
        820       830       840       850       860

P  A  K  T  L  V  E  K  E  A  E  E  S  T
CAGCAAAAACTTTGGTTGAAAAAGAGGCAGGAGAAAGTAC
        870       880       890       900

Q  V  Y  P  K  F  V  F  D  D  Y  M  K  L  Y  A
ACAAGTGTATCCAAAGTTTGTGTTTGATGATTACATGAAGTTATATGCTG
        910       920       930       940       950

G  L  K  F  Q  A  K  E  P  R  F  E  A  M
GACTCAAGTTTCAAGCCAAAGAGAGCCAAGATTTGAAGCAAT
        960       970       980       990

K  A  M  E  S  D  P  I  A  S  A  *
GAAGGCAATGGAAAGTGATGATCCAATTGCAAGTGCTTAGATCCCAATTCAAT
        1000      1010      1020      1030      1040

TAAAAAAATTGGTGTGTTTGAAAAATATATTTAAATATAGCA
        1050      1060      1070      1080
```

DNA CONSTRUCTS CONTAINING THE GENE FOR ACC OXIDASE, CELLS AND PLANTS DERIVED THEREFROM

This is a continuation of application Ser. No. 07/793,450, filed as PCT/GB90/01072,Jul. 12, 1990, now U.S. Pat. No. 5,365,015.

This application relates to novel DNA constructs, plant cells containing them and plants derived therefrom. In particular it involves the use of antisense RNA technology to control gene expression in plants.

As is well known, a cell manufactures protein by transcribing the DNA of the gene for that protein to produce messenger RNA (mRNA), which is then processed (eg by the removal of introns) and finally translated by ribosomes into protein. Translation may be inhibited by the presence in the cell of "antisense RNA". By this term is meant an RNA sequence which is complementary to a sequence of bases in the mRNA in question: complementary in the sense that each base in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or degrade the mRNA, or have more than one of these effects. Such antisense RNA may be produced in a cell by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes has been described, in for example European Patent publication no 271988 to ICI (corresponding to U.S. Ser. No. 119614). Reduction in gene expression has led to a change in the phenotype of the plant: either at the level of gross visible phenotypic difference e.g. lack of anthocyanin production in flower petals of petunia leading to colourless instead of coloured petals (van der Krol et al, Nature, 333, 866–869, 1988); or at a more subtle biochemical level e.g. change in the the amount of polygalacturonase and reduction in depolymerisation of pectins during tomato fruit ripening (Smith et al, Nature, 334, 724–726, 1988; Smith et al., Plant Mol. Biol., 14, 1990, 369–379). Thus antisense RNA has been proven to be useful in achieving downregulation of gene expression in plants.

The present invention is based on two discoveries: that a known gene of hitherto unknown function is involved in the ethylene biosynthesis pathway; and that RNA antisense to this gene is effective in disrupting this pathway and reducing ethylene production. The gene in question is encoded (almost completely) in pTOM13, disclosed in Holdsworth et al., Nucleic Acids Research, 15, 731–739, 1987.

According to the present invention we provide DNA constructs comprising a DNA sequence homologous to some or all of a gene encoding an enzyme involved in ethylene biosynthesis, preceded by a transcriptional initiation region operative in plants, so that the construct can generate RNA in plant cells.

In a further aspect the invention comprises DNA constructs comprising a transcriptional initiation region operative in plants positioned for transcription of a DNA sequence encoding RNA complementary to a substantial run of bases showing substantial homology to an mRNA encoding an enzyme involved in ethylene biosynthesis. Preferably the mRNA encoding the enzyme involved in ethylene biosynthesis derives from DNA from pTOM13; or from DNA which is fully or partly homologous thereto. The invention also includes plant cells comprising constructs according to the invention; plants derived therefrom showing reduced ethylene production; and seeds of such plants.

Two principal enzymes involved in ethylene biosynthesis in plants are ACC Synthase and ACC Oxidase. We believe that pTOM13 contains DNA coding for the latter. Whether this is so or not, pTOM13 is certainly an effective source of DNA for use in inhibiting ethylene production according to the present invention. See the paper in "Nature", Vol. 346, Jul. 19, 1990, pages 284–287, of which the present inventors are authors.

The constructs of the invention may be inserted into plants to regulate the production of ethylene. Depending on the nature of the construct, the production of ethylene may be increased, or reduced, either throughout or at particular stages in the life of the plant. Generally, as would be expected, production of ethylene is enhanced only by constructs which express RNA homologous to a substantially complete endogenous mRNA involved in the ethylene pathway. What is more surprising is that constructs containing an incomplete DNA sequence substantially shorter than that corresponding to a complete gene generally inhibit the expression of the gene and hence production of ethylene, whether they are arranged to express sense or antisense RNA.

Plants showing reduced ethylene production have a variety of useful properties. Amongst other effects, reduction of ethylene can find use in delaying fruit ripening; fruit softening; fruit, leaf and flower senescence; and fruit, leaf and flower abscission.

DNA constructs according to the invention preferably comprise a base sequence at least 50 bases in length for transcription into antisense RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

The preferred source of antisense RNA for use in the present invention is DNA showing homology to the gene encoded by the clone pTOM13.

The required antisense DNA can be obtained by cutting with restriction enzymes an appropriate sequence of such DNA; and then cloning the cut DNA into a vector containing upstream promoter and downstream terminator sequences, the cloning being so carried out that the cut DNA sequence is inverted with respect to its orientation in the strand from which it was cut.

In the new vector, the strand that was formerly the template strand becomes the coding strand, and vice versa. The new vector will thus produce RNA in a base sequence which is complementary to the sequence of pTOM13 mRNA. Thus, the two RNA strands are complementary not only in their base sequence but also in their orientations (5' to 3').

As source of the DNA base sequence for transcription, it is convenient to use a cDNA clone such as pTOM13. The base sequence of pTOM13, as deduced from sequencing the RNA it produces, is set out in FIG. 1. pTOM13 has been deposited on 6 Jul. 1989 with the National Collections of Industrial and Marine Bacteria, Aberdeen, under Accession No. NCIB 40162. Alternatively, a cDNA clone similar to pTOM13 may be obtained from the mRNA of ripening tomatoes by the method described by Slater et al, Plant Molecular Biology 5, 137–147. In this way may be obtained sequences coding for the whole, or substantially the whole, of the mRNA produced by pTOM13. Suitable lengths of the cDNA so obtained may be cut out for use by means of restriction enzymes.

An alternative source of DNA for the base sequence for transcription is a suitable gene encoding a protein involved in ethylene biosynthesis. Such a gene will differ from the cDNA of, eg. pTOM13, in that introns are present. The introns are not transcribed into mRNA (or, if so transcribed, are subsequently cut out). When using such a gene as the source of the base sequence for transcription it is possible to use either intron or exon regions.

Genes or cDNA for use in the invention may be isolated from other sources besides tomatoes: for example, from ripening fruit such as peaches or melons. For this purpose it is convenient to use DNA derived from pTOM13 as a probe.

A further way of obtaining a suitable DNA base sequence for transcription is to synthesise it ab initio from the appropriate bases, for example using FIG. 1 as a guide, or the published sequence of GTOMA (Holdsworth et al., Nucleic Acids Research, 15, 10600, 1987).

Recombinant DNA and vectors according to the present invention may be made as follows. A suitable vector containing the desired base sequence for transcription (for example pTOM13) is treated with a restriction enzyme to cut the sequence out. The DNA strand so obtained is cloned (in reverse orientation) into a second vector containing the desired promoter sequence (for example CaMV 35S or the polygalacturonase gene promoter sequence—Bird et al., Plant Molecular Biology, 11, 651–662, 1988) and the desired terminator sequence (for example the 3' end of the nopaline synthase gene, the nos 3' end).

According to the invention we propose to use both constitutive promoters (such as CaMV and inducible or developmentally regulated promoters (such as that for the polygalacturonase gene, or abcission-zone-specific or flower-specific promoters) as circumstances require. Use of a constitutive promoter will tend to affect all functions controlled by ethylene: while by use of an inducible promoter functions may be controlled more selectively. Thus in applying the invention, eg to tomatoes, it may be found convenient to use the promoter of the PG gene (Bird et al., 1988, cited above). Use of this promoter, at least in tomatoes, has the advantage that the production of antisense RNA is under the control of a ripening-specific promoter. Thus ethylene production will only be inhibited during fruit ripening and not in other stages of development. Another ripening-specific inducible promoter that could be used is the E8 promoter (Diekman & Fischer, EMBO Journal 7, 3315–3320, 1988)

Vectors according to the invention may be used to transform plants as desired, to make plants according to the invention. Dicotyledonous plants, such as the tomato, may be transformed by Ti plasmid technology, for example as described by Bevan (1984) Nucleic Acid Research, 12, 8711–8721. Such transformed plants may be reproduced sexually, or by cell culture.

The degree of production of antisense RNA in the plant cells can be controlled by suitable choice of promoter sequences, or by selecting the number of copies, or the site of integration, of the DNA sequences according to the invention that are introduced into the plant genome. In this way, for example, it may prove possible to delay softening of tomatoes for a greater or lesser period after ripening.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which can subsequently reproduce to give successive generations of genetically modified plants. Preferred genetically modified plants according to the present invention are climacteric fruit, including, as well as tomatoes, fruits such as mangoes, peaches, apples, pears, bananas and melons.

As previously stated, the preferred source of antisense RNA for use in the present invention is DNA showing homology to the gene encoded by the clone pTOM13. pTOM13 was derived from a cDNA library isolated from red tomato RNA. We have characterised it by in vitro hybrid-select translation (Slater et al, Plant Molecular Biology 5, 137–147 describes the method) and have shown that it encodes a protein of approximately 35,000 daltons. DNA sequence analysis has demonstrated that the clone is 1370 bases long. It is believed to encode a cytoplasmic protein, as no apparent leader sequence was detected using computer analysis of the amino acid sequence derived from the DNA sequence. However, the assignment of this protein as a cytoplasmic protein is speculative as it is not clearly known which targeting information is required for directing proteins to the tonoplast or vacuole.

We have shown that the mRNA for which pTOM13 codes is induced very rapidly after mechanical wounding to tomato leaves, as well as in tomato fruit during ripening. After wounding, maximal expression was observed one hour after wounding with mRNA increases detectable as early as 10 minutes after wounding. After 3 hours, pTOM13 mRNA levels had declined to levels observed before wounding.

In tomato fruit, pTOM13 mRNA is expressed most strongly at the full orange stage of ripening. The level of mRNA then declines in line with the general decline in biosynthetic capacity of the ripening fruit. Wounded fruit also respond by producing pTOM13 mRNA. However, the levels of induction vary: they are greatest in green wounded fruit, and virtually non-existent in led wounded fruit.

The gene copy number of pTOM13 has been analysed using various techniques. The genomic location of pTOM13 has been identified using RFLP mapping (Mutschler et al., Theoretical and Applied Genetics 76, 285–292, 1988): two loci in the tomato genome carry sequences homologous to pTOM13. It has also been shown by Southern blotting that the gene is present as a small multigene family, consisting of 3–4 members. Some members of this gene family have been cloned and the sequence of three of these determined (Holdsworth et al., Plant Molecular Biology 11, 81–88, 1988). GTOM17 is homologous to pTOM13 and is expressed in the wounded leaf, wounded fruit and during fruit ripening. GTOMA is closely related but not identical to pTOM13 and is expressed in wounded leaves. A third gene, GTOMB, is probably a pseudogene. Sequence analysis of these clones and searches in DNA and protein databases has not revealed homology to any known proteins.

Although this considerable body of information on the structure and expression of the pTOM13 gene family is known, the biochemical function of this clone has not hitherto been elucidated. It has been suggested (Holdsworth et al., Nucleic Acids Research, 15, 731–739, 1987; Smith et al., Planta 168, 94–100, 1986) that the clone may be involved in ethylene biosynthesis or metabolism. This suggestion has been arrived at from the apparent relationship between ethylene biosynthesis and evolution with pTOM13 expression. However there was hitherto no evidence for the biochemical function of proteins encoded by this gene family. Nor has such evidence been obtained by other workers, who have isolated a clone closely related to pTOM13, namely E8 (Deikman et al., EMBO Journal 7, 3315–3320, 1988)

In work leading to the present invention, we used antisense RNA in order to determine the phenotype of transgenic tomato plants which show reduced expression of pTOM13. The results (which could not have been predicted) of the experiments described below demonstrate that the use of antisense RNA to pTOM13 leads to a reduction in ethylene production. This can be shown in wounded leaf tissue, in wounded green fruit and in ripening tomato fruit tissue.

The reduction in ethylene observed in primary transformants varied from 50%–95%. As such transformants typically contain the construct in only one allele, by selfing the plants and selecting those offspring which contain the construct in both alleles we can obtain plants in which ethylene production is further reduced or even substantially completely inhibited. Thus according to the invention we can generate plants which have a range of levels of ethylene production, as desired.

This invention can be used to control tomato fruit ripening and softening, as well as plant growth and flower and fruit development of many flowering plants. Reduction in ethylene levels in plants will delay such phenomena, particularly fruit development and fruit softening, including rate of pigment formation as well as the induction of cell wall changes. The effect of these changes will be prolonged ripening time and storage life of fruit. Overripening as seen in many fruits (including, for example, tomatoes, mangoes, peaches, apples, pears, bananas and melons) may be prevented. It is expected that leaf senescence could be delayed, allowing the creation of leaf vegetables (eg lettuce, cabbage, spinach) that will stay green longer. We also expect that flower petal senescence and abscission will be delayed. This could find use in the horticultural industry, leading to cut flowers (roses, chrysanthemums, carnations, tulips, daffodils, etc) and pot plants having a longer shelf life.

Since the constructs of the invention act in the transformed plants by reducing the production of ethylene, their effects may be wholly or partially reversed, at will, by supplying ethylene to the plants. At present, fruit (eg tomatoes, bananas) are transported to the point of sale under refrigeration to prevent ripening, and there ripened by application of ethylene. Fruit according to the present invention would not need to be refrigerated (saving energy and expense, and protecting the ozone layer). Ethylene may be applied as the free gas, or in the form of ethylene-generating compounds, such as ethephon.

As ethylene is involved in plant wounding responses, we expect plants containing the constructs of the present invention to have novel responses to wounding. They may, for example, be found to be more susceptible to wounding (though we have yet to observe any such difference in transformed tomatoes). It is also possible that lower production of ethylene in response to wounding may be associated with less active microbial attack, with consequent improved fresh storage qualities.

The invention will now be described further with reference to the accompanying drawings, in which:

FIGS. 1A–D show the base sequence of the clone pTOM13;

Figure 4A:
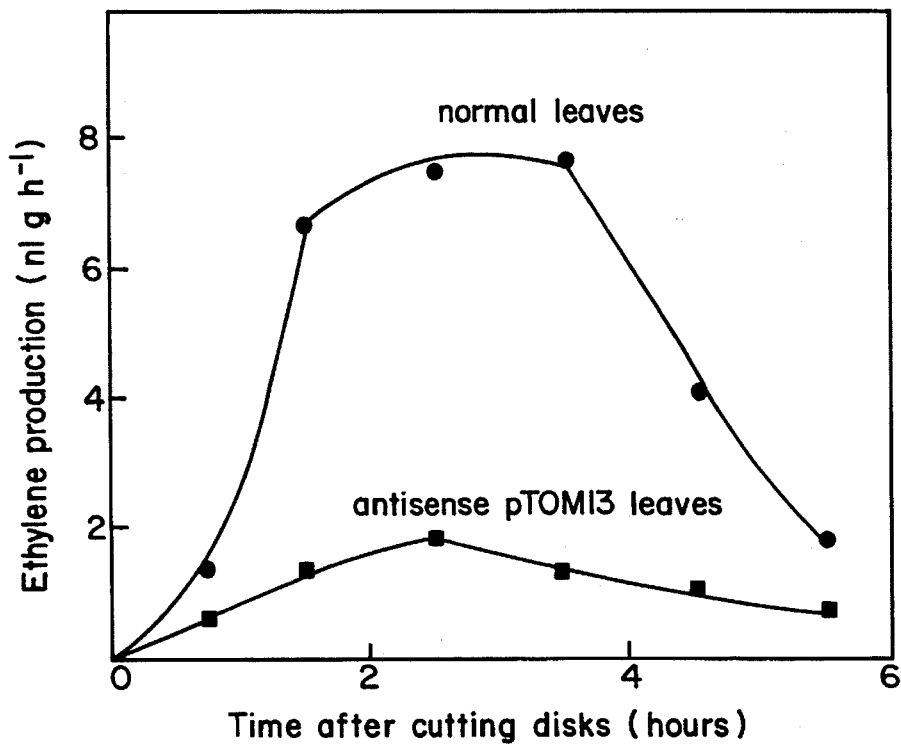
Figure 4B:
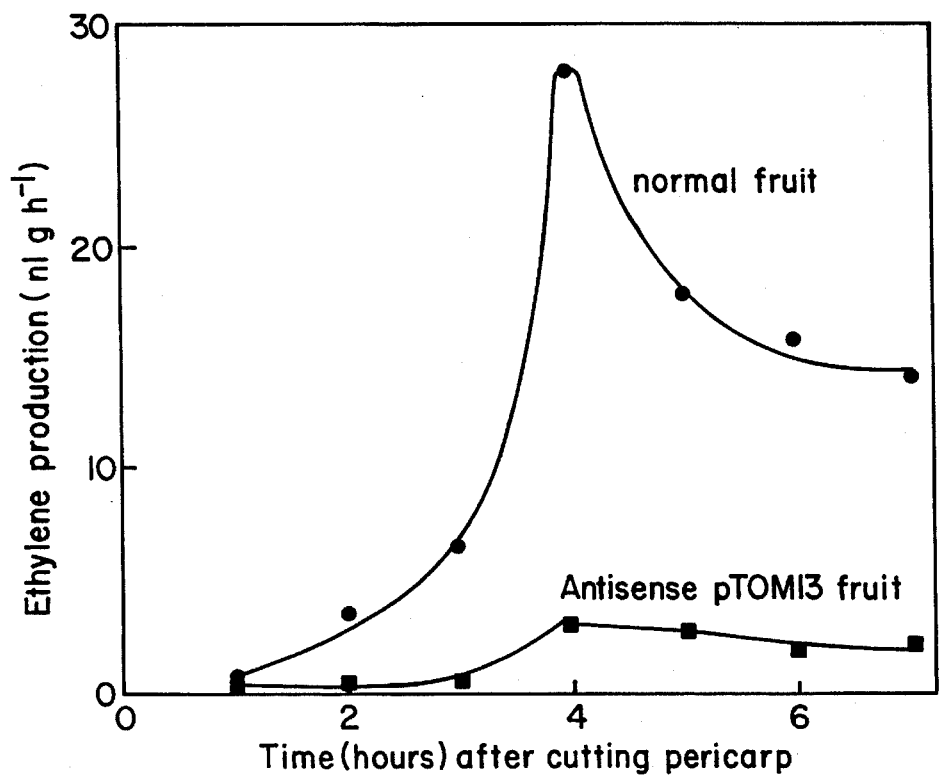
Figure 4C:
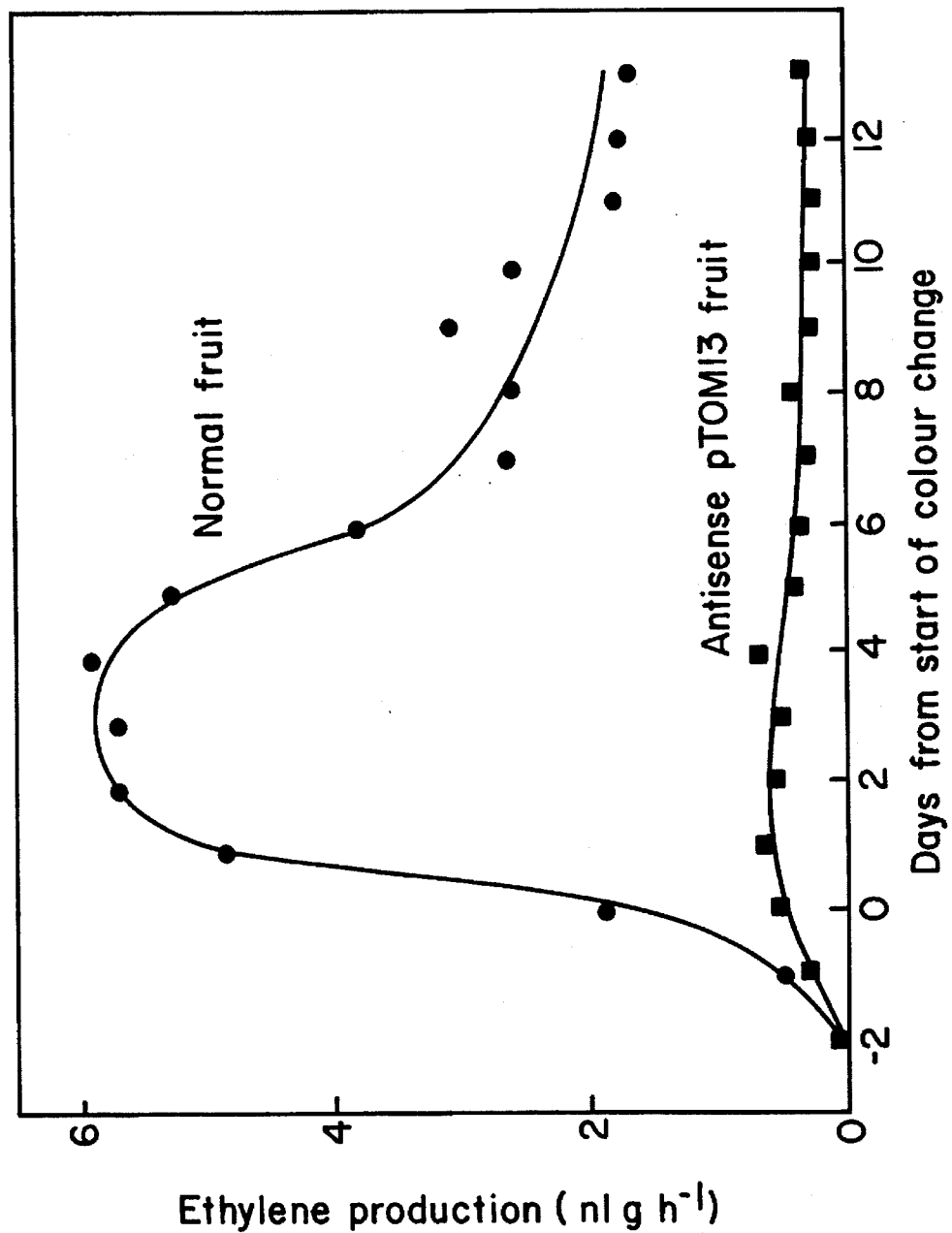

FIGS. 4a–4c show how ethylene production varies over time in tissue of control and transgenic tomato plants (FIG. 4a: wounded leaves; FIG. 4b: wounded green fruit; FIG. 4c: unwounded ripening fruit)

Figure 5:
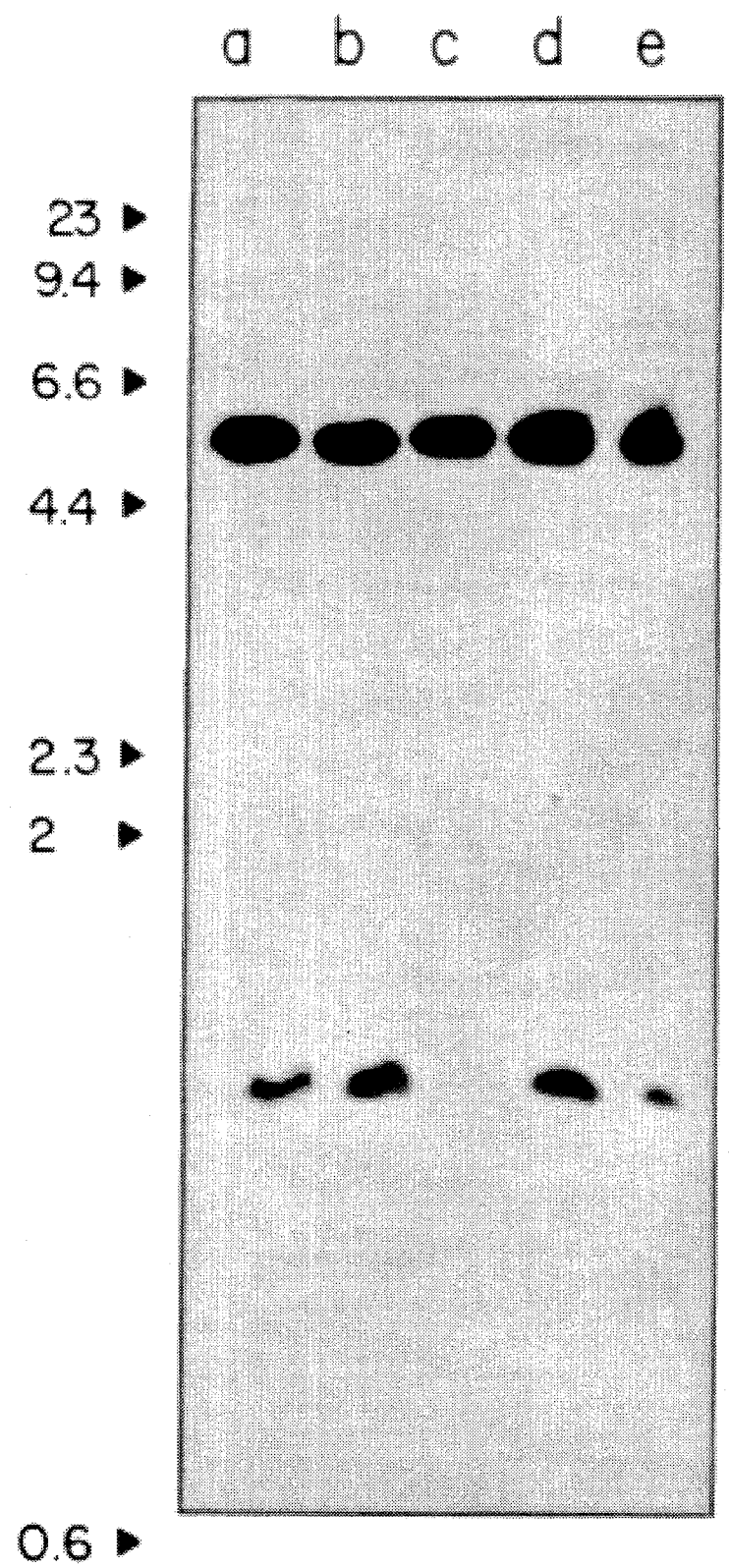

FIG. 5 is an autoradiograph of Southern blots of five F1 tomato plants obtained by selfing transgenic tomato plants from Example 3.

The following Examples illustrate aspects of the invention.

EXAMPLE 1

Correct Identification of Base Sequence of pTOM13

The sequence of pTOM13 has previously been published (Holdsworth et al., Nucleic Acids Research, 15, 731–739, 1987). During the construction of antisense RNA vectors, we identified considerable sequence homology between the 5' and 3' ends of pTOM13. We therefore decided to sequence the pTOM13 mRNA found in the ripening fruit. The, correct sequence of a cDNA clone encoding pTOM13 RNA as determined by RNA sequencing is shown in FIGS. 1A–D.

It is important to recognise that the previously published sequence differs at the 5' end of the mRNA. As this may be the region particularly useful in the construction of antisense RNA vectors, it is especially important to have identified the correct RNA/cDNA sequence.

EXAMPLE 2

Construction of pTOM13 Antisense RNA Vectors

Two sets of vectors were constructed.

1. using the complete pTOM13 cDNA (pBAS)
2. using pTOM13 cDNA minus the last 200 bases (pBASC)

These fragments were cloned separately into pDH51, a pUC based vector, which permits the expression of antisense RNA under the control of the CaMV 35S promoter. This vector uses a CaMV 3' end sequence. The orientation of the pTOM13 sequences was determined using restriction mapping and DNA sequence determination of the borders of the cDNA and the vector sequences. After verification of the structure of these vectors, the expression module was transferred to Bin19 (Bevan, Nucleic Acid Research, 12, 8711–8721, 1984) using standard cloning protocols.

Figure 2A:
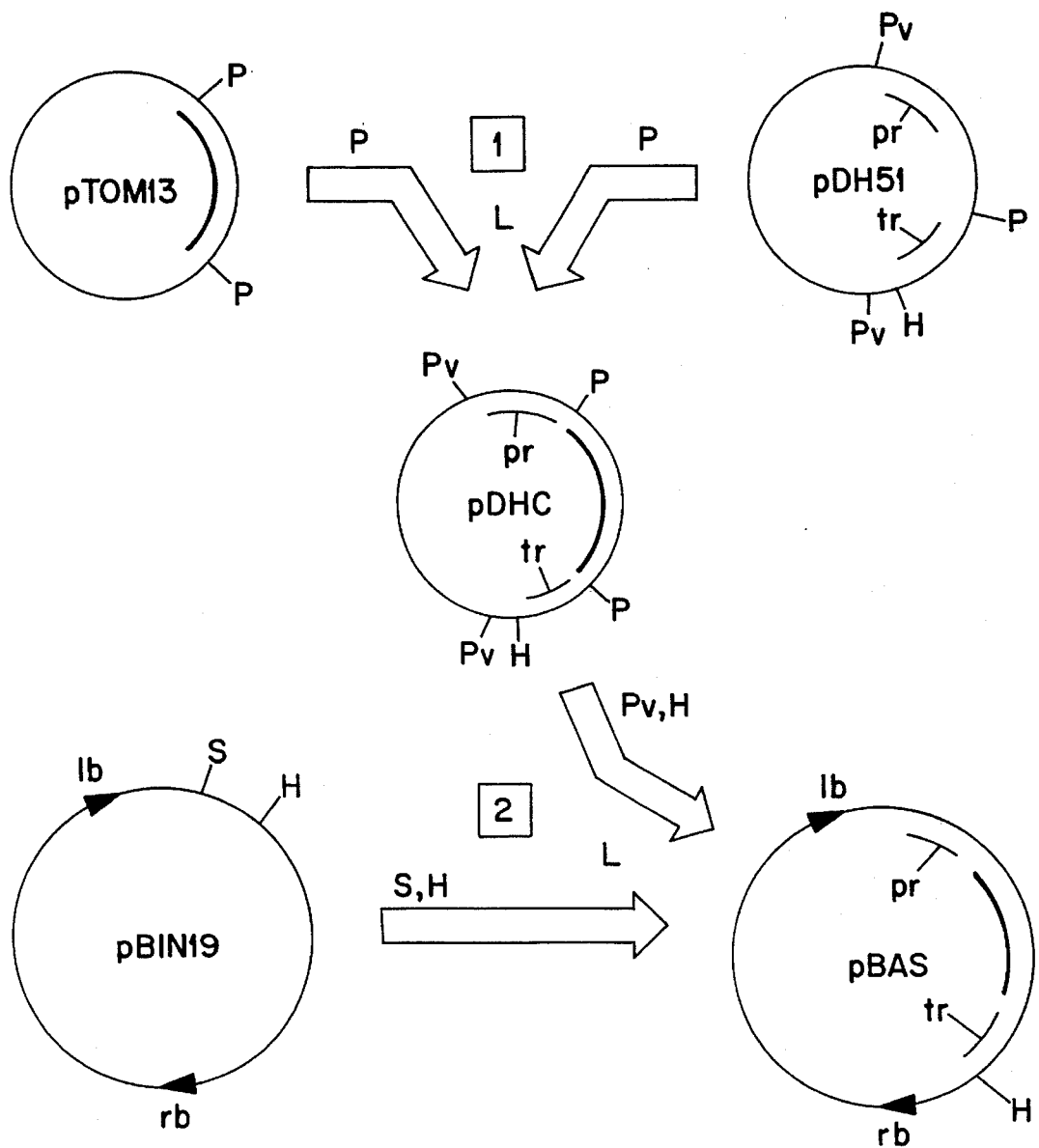
FIG. 2a illustrates diagrammatically the construction of a pTOM13 antisense vector pBAS according to the invention.

FIG. 2a shows in more detail the construction of a pTOM13-antisense plant transformation vector, pBAS. The 1.3 Kb cDNA insert was cut by Pst 1 from pTOM13 and ligated into the Pst 1 site of pDH51 (step 1). The expression unit with the insert in the antisense orientation with respect to the promoter (pr) was transferred to the multiple cloning site between the left and right T-DNA borders of the plant transformation binary vector, Bin 19 (step 2) to create pBAS.

Figure 2B:
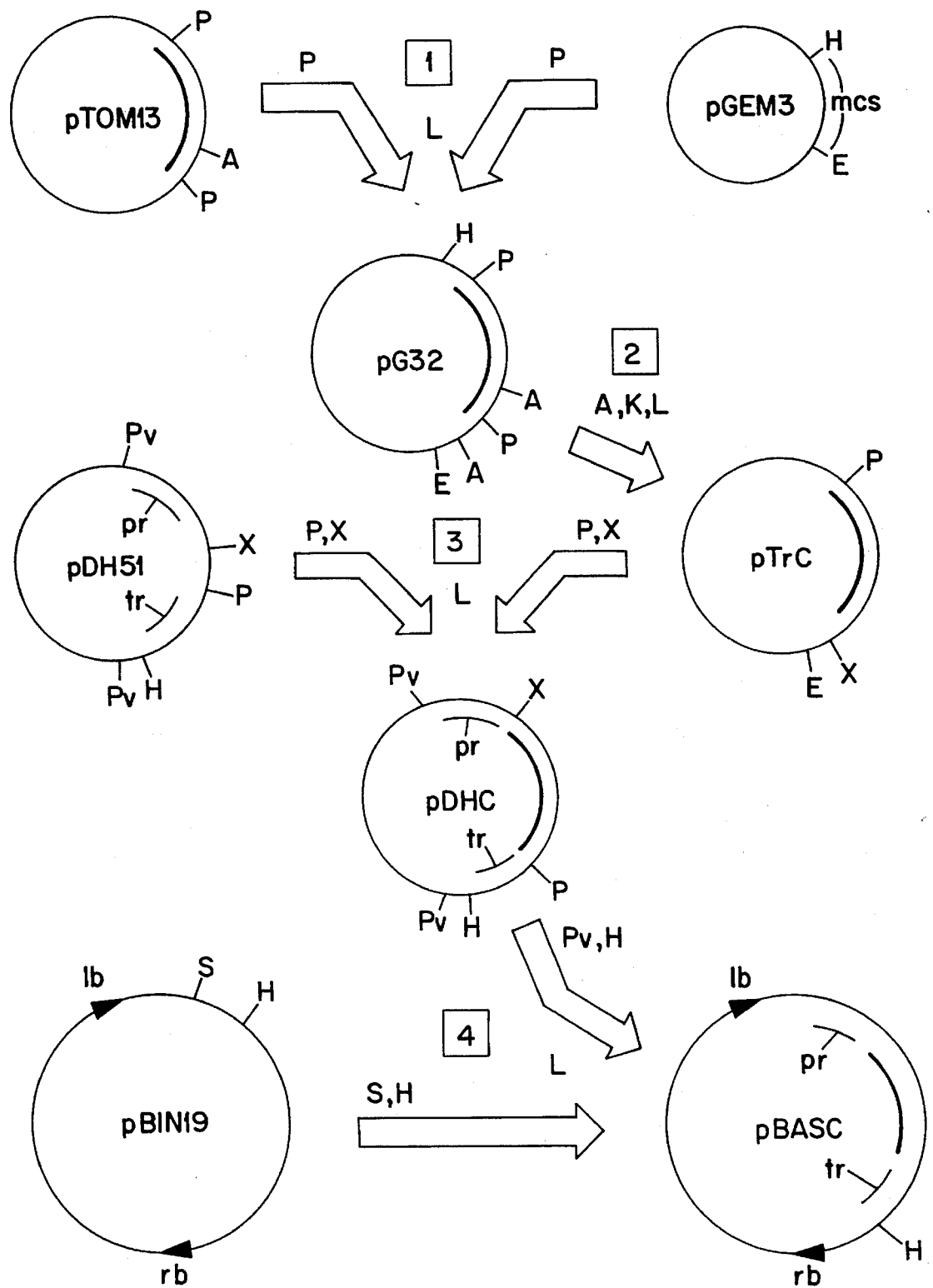
FIG. 2b illustrates diagrammatically the construction of a truncated pTOM13 antisense plant transformation vector pBASC according to the invention.

FIG. 2b shows in more detail the construction of the truncated pTOM13-antisense plant transformation vector, pBASC. The 1.3 Kb cDNA insert was cut by Pst 1 from pTOM13 and ligated into the Pst 1 site in pGEM3 (Promega Biotech, Madison, U.S.A.) (step 1). A 200 bp Acc 1 fragment was deleted from the 3' end of the cDNA (step 2). A Pst 1-Xbal fragment containing the truncated cDNA was ligated in the antisense orientation between the 35S promoter and terminator of pDH51 (step 3). This "expression unit" was transferred to the multiple cloning site between the left and right T-DNA borders of the plant transformation binary vector, Bin 19 (step 4) to create pBASC.

The following abbreviations are used in FIGS. 2a and 2b: P, Pst 1; A, Acc 1; L, T4 DNA ligase; H, Hind III; E, ECO R1; K, Klenow fragment of E. coli DNA polymerase; X, Xbal; Pv, Pvu11; pr, 35S promoter; tr, 35S terminator; lb, rb, left and right T-DNA border repeats; S, Sma 1; mcs, multiple cloning site.

EXAMPLE 3

Generation of Transformed Plants

Vectors were transferred to Agrobacterium LBA4044 (a microorganism strain widely available to plant biotechnologists) and were used in transformation experiments. Transformation of stem segments and leaf disks for tomato and tobacco respectively followed standard protocols. Transformed plants were identified by their ability to grow on kanamycin-containing media.

EXAMPLE 4

Analysis of Transformed Tomato Plants

I. DNA Analysis of Transformed Plants

DNA was extracted from leaves of transformed plants. Southern analysis of this DNA confirmed the presence of the antisense genes in a number of plants. , II. Analysis of Leaf Samples of Transformed Plants II.1 RNA analysis RNA was extracted from leaves of transformed plants and probed with strand-specific probes to pTOM13. This indicated that antisense RNA was synthesised in the transgenic plants.

Figure 3A:
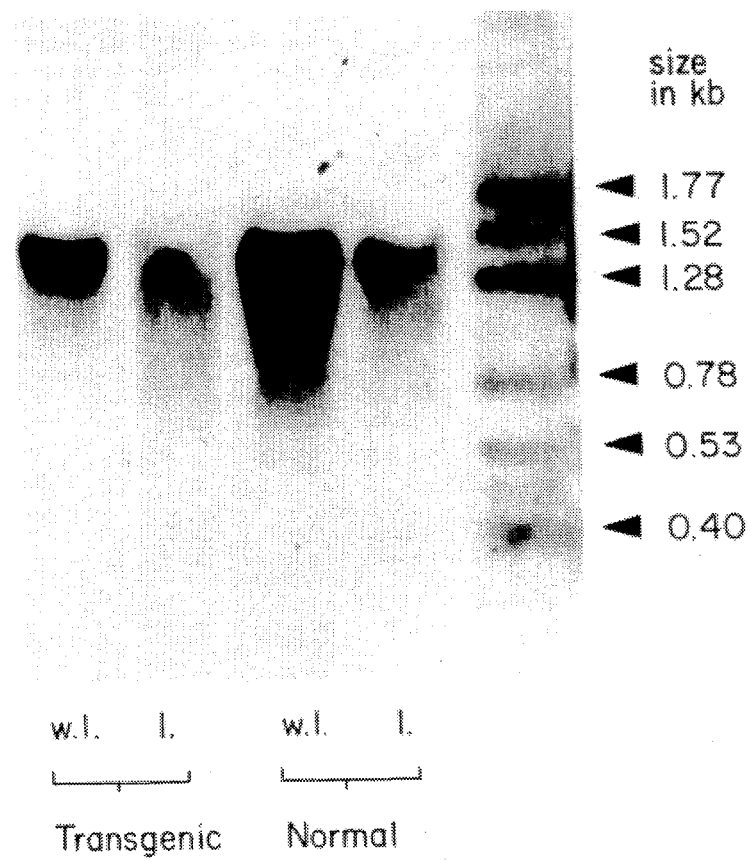
FIG. 3 shows autoradiographs of Northern hybridisations detecting the expression of pTOM13 sense and antisense RNA in tissue of control and transgenic tomato plants (wounded and unwounded leaves)
Figure 3B:
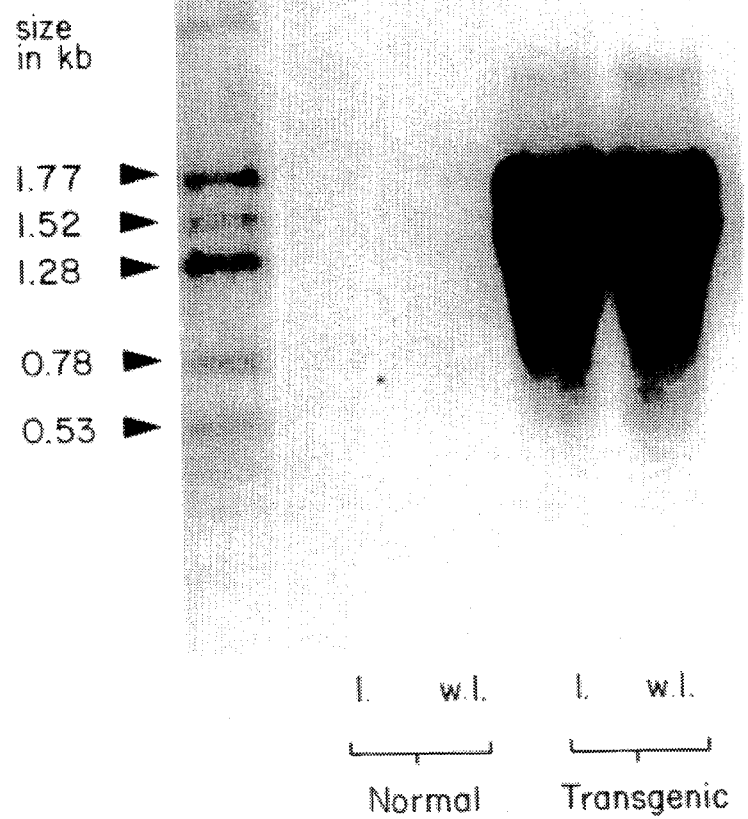

After wounding, a considerable amount of pTOM13 mRNA accumulated. In transformed plants this accumulation was inhibited. A reduction of approximately 50–80% of pTOM13 mRNA was observed. This is illustrated in FIG. 3, which shows the measurement of the amount of pTOM13 mRNA and antisense RNA in wounded leaves of normal and transgenic antisense plants by Northern hybridisation analysis. RNA was extracted from unwounded and wounded leaves (marked l. and w.l., respectively, in FIG. 3); fractionated by agarose gel electrophoresis; blotted onto hybridisation membranes; and challenged with sense-specific (A in FIG. 3) or antisense-specific probes (B in FIG. 3).

II.2 Ethylene measurements

Ethylene production was measured on:

(a) wounded leaves (b) wounded green fruit (c) unwounded ripening fruit;

of tomato by standard methods of gas chromatography using an alumina column. A reduction of 80% or more in ethylene evolution occurred in wounded transgenic plants when compared to untransformed wild-type controls. FIG. 4 shows how the evolution of ethylene from tissues of normal plants and antisense plants varies with time (FIG. 4a: wounded leaf discs; FIG. 4b: wounded segments cut from green (unripe) fruit pericarp; FIG. 4c: unwounded ripening fruit)

III. Analysis of transformed tomato fruit.

1. RNA analysis

RNA was extracted from normal and transformed tomato fruit (obtained from Example 3) at different ripening stages. The levels of pTOM13 mRNA were determined by Northern hybridisation analysis. In this (single) experiment, no pTOM13 mRNA was detected in ripening fruit of antisense plants.

2. Ethylene analysis.

Fruit from transformed tomato plants (from Example 3) containing the antisense constructs of the invention showed a reduction in the level of ethylene present during fruit ripening of 80% or more. FIG. 4c shows how ethylene production varies with time in ripening fruit (normal and antisense). Ethylene production is reduced in the antisense fruit.

EXAMPLE 5

Identification of Homozygous Antisense Gene Tomato Plants

Selfed progeny of the original transformants from Example 3 were generated, and homozygous plants identified by Southern blot analysis, using as probes DNA obtained from pTOM13. FIG. 5 is an autoradiograph of genomic Southern hybridisation of DNA from F1 generation plants from a parent transformed with the antisense-pTOM13 plant transformation vector pBASC (from Example 2). DNA was extracted from leaves, digested with ECO R1, fractionated by agarose gel electrophoresis, blotted onto a hybridisation membrane and challenged with a random prime 32p-labelled pTOM13 cDNA insert probe. The results indicate plants with 1 (tracks a,e), 2 (tracks b,d) and 0 (track c) pTOM13-antisense genes. Molecular weight markers are shown in kilobases on the left of the Figure. The plants of tracks b and d are thus thought to be homozygous for the antisense construct, which it seems is segregating in a normal Mendelian fashion.

Seeds of the homozygous tomato plants were deposited at the National Collections of Industrial and Marine Bacteria, 23 St. Machar Drive, Aberdeen AB2 1RY, Scotland, on 10 Jul. 1990 under the reference number NCIB 40307.

We claim:

1. A recombinant construct comprising a DNA sequence corresponding to the DNA sequence of a gene encoding the enzyme ACC oxidase preceded by a transcriptional initiation region operative in plants such that the construct can generate RNA in plant cells and thereby reduce expression of said enzyme with consequent inhibition of ethylene production in plants.

2. The construct of claim 1 wherein the transcriptional initiation region operative in plants is positioned to produce mRNA complementary to mRNA encoding the enzyme ACC oxidase.

3. The construct of claim 1 wherein the transcriptional initiation region operative in plants is a constitutive promoter.

4. The construct of claim 3 wherein the constitutive promoter is CaMV 35S.

5. The construct of claim 1 wherein the transcriptional initiation region operative in plants is an inducible or developmentally regulated promoter.

6. The construct of claim 5 wherein the promoter is that for a polygalacturonase gene.

7. The construct of claim 1 wherein the DNA sequence has sequence identity with pTOM 13.

8. A method of modifying the production of ACC oxidase in plants which comprises transforming plant cells with a DNA construct according to claim 1.

9. A method according to claim 8 wherein the DNA sequence in said construct has sequence identity with pTOM 13.

10. A method according to either claim 8 or 9 wherein the DNA sequence in said construct is oriented in the antisense direction.

11. Plant cells transformed with a construct according to any one of claims 1–7 in which ethylene production is reduced compared to non-transformed plant cells.

12. Plants derived from plant cells according to claim 11 or seeds obtained from such plants.

13. Plants derived from plant cells according to claim 11, said plants being selected from the group consisting of tomatoes, mangoes, peaches, apples, pears, bananas, melons, lettuce, cabbage, spinach, roses, chrysanthemums, carnations, tulips and daffodils.

14. A genetically modified tomato plant, derived from plant cells transformed with a construct according to any one of claim 1–7 exhibiting a reduction in ethylene expression of at least 50%.

15. The genetically modified tomato plant of claim 14, wherein ethylene expression is reduced between 50% and 95%.

* * * * *